United States Patent
Hoey et al.

(10) Patent No.: US 10,335,222 B2
(45) Date of Patent: Jul. 2, 2019

(54) INDUCTION COIL VAPOR GENERATOR

(71) Applicant: NxThera, Inc., Maple Grove, MN (US)

(72) Inventors: Michael Hoey, Shoreview, MN (US); Roger Noel Hastings, Maple Grove, MN (US); Stephanos Paulos, Little Canada, MN (US)

(73) Assignee: NxThera, Inc., Maple Grove, MN (US)

( * ) Notice: Subject to any disclaimer, the term of this patent is extended or adjusted under 35 U.S.C. 154(b) by 890 days.

(21) Appl. No.: 14/384,774

(22) PCT Filed: Apr. 3, 2013

(86) PCT No.: PCT/US2013/035144
§ 371 (c)(1),
(2) Date: Sep. 12, 2014

(87) PCT Pub. No.: WO2013/152119
PCT Pub. Date: Oct. 10, 2013

(65) Prior Publication Data
US 2015/0025515 A1    Jan. 22, 2015

Related U.S. Application Data

(60) Provisional application No. 61/619,818, filed on Apr. 3, 2012.

(51) Int. Cl.
*A61B 18/04* (2006.01)
*F22B 1/28* (2006.01)
*A61B 18/00* (2006.01)

(52) U.S. Cl.
CPC .............. *A61B 18/04* (2013.01); *F22B 1/281* (2013.01); *A61B 2018/00083* (2013.01);
(Continued)

(58) Field of Classification Search
CPC .......... A61B 18/04; A61B 2018/00083; A61B 2018/00101; A61B 2018/00547; A61B 2018/00577; A61B 2018/048
(Continued)

(56) References Cited

U.S. PATENT DOCUMENTS

| 408,899 A | 8/1889 | Small |
| 1,719,750 A | 7/1929 | Bridge et al. |

(Continued)

FOREIGN PATENT DOCUMENTS

| CN | 2061443 U | 9/1990 |
| CN | 2418844 Y | 2/2001 |

(Continued)

OTHER PUBLICATIONS

US 5,326,343 A, 07/1994, Rudie et al. (withdrawn)
(Continued)

*Primary Examiner* — Michael F Peffley
*Assistant Examiner* — Khadijeh A Vahdat
(74) *Attorney, Agent, or Firm* — Bookoff McAndrews, PLLC

(57) ABSTRACT

An induction coil vapor generator is provided that may include any of a number of features. One feature of the vapor generator is that it can inductively generate high quality condensable vapor. The vapor generator can comprise an outer assembly that supports a coil wire, and an inner assembly disposed in the outer assembly. The inner assembly can house a plurality of microtubes configured to be inductively heated by the coil wire to convert a fluid to condensable vapor. The generator can be disposed in a medical device to treat tissue with vapor. One feature of the medical device is that it can apply condensable vapor energy
(Continued)

to tissue, such as a prostrate, to shrink, damage, denaturate the prostate. Methods associated with use of the vapor generator are also covered.

17 Claims, 8 Drawing Sheets

(52) U.S. Cl.
CPC .............. *A61B 2018/00101* (2013.01); *A61B 2018/00547* (2013.01); *A61B 2018/00577* (2013.01); *A61B 2018/048* (2013.01)

(58) Field of Classification Search
USPC .................................................. 606/21–41
See application file for complete search history.

(56) References Cited

U.S. PATENT DOCUMENTS

| | | |
|---|---|---|
| 4,672,963 A | 6/1987 | Barken |
| 4,920,982 A | 5/1990 | Goldstein |
| 4,950,267 A | 8/1990 | Ishihara et al. |
| 5,117,482 A | 5/1992 | Hauber |
| 5,222,185 A | 6/1993 | McCord, Jr. |
| 5,249,585 A | 10/1993 | Turner et al. |
| 5,300,099 A | 4/1994 | Rudie |
| 5,312,399 A | 5/1994 | Hakky et al. |
| 5,330,518 A | 7/1994 | Neilson et al. |
| 5,366,490 A | 11/1994 | Edwards et al. |
| 5,370,609 A | 12/1994 | Drasler et al. |
| 5,370,675 A | 12/1994 | Edwards et al. |
| 5,370,677 A | 12/1994 | Rudie et al. |
| 5,385,544 A | 1/1995 | Edwards et al. |
| 5,409,453 A | 4/1995 | Lundquist et al. |
| 5,413,588 A | 5/1995 | Rudie et al. |
| 5,421,819 A | 6/1995 | Edwards et al. |
| 5,435,805 A | 7/1995 | Edwards et al. |
| 5,464,437 A | 11/1995 | Reid et al. |
| 5,470,308 A | 11/1995 | Edwards et al. |
| 5,470,309 A | 11/1995 | Edwards et al. |
| 5,484,400 A | 1/1996 | Edwards et al. |
| 5,499,998 A | 3/1996 | Meade |
| 5,531,676 A | 7/1996 | Edwards et al. |
| 5,531,763 A | 7/1996 | Mastri et al. |
| 5,542,915 A | 8/1996 | Edwards et al. |
| 5,542,916 A | 8/1996 | Hirsch et al. |
| 5,545,171 A | 8/1996 | Sharkey et al. |
| 5,549,644 A | 8/1996 | Lundquist et al. |
| 5,554,110 A | 9/1996 | Edwards et al. |
| 5,556,377 A | 9/1996 | Rosen et al. |
| 5,558,673 A | 9/1996 | Edwards et al. |
| 5,588,960 A | 12/1996 | Edwards et al. |
| 5,591,125 A | 1/1997 | Edwards et al. |
| 5,599,294 A | 2/1997 | Edwards et al. |
| 5,601,591 A | 2/1997 | Edwards et al. |
| 5,628,770 A | 5/1997 | Thome et al. |
| 5,630,794 A | 5/1997 | Lax et al. |
| 5,645,528 A | 7/1997 | Thome |
| 5,667,488 A | 9/1997 | Lundquist et al. |
| 5,672,153 A | 9/1997 | Lax et al. |
| 5,709,680 A | 1/1998 | Yates et al. |
| 5,720,718 A | 2/1998 | Rosen et al. |
| 5,720,719 A | 2/1998 | Edwards et al. |
| 5,776,176 A | 7/1998 | Rudie |
| 5,792,070 A | 8/1998 | Kauphusman et al. |
| 5,797,903 A | 8/1998 | Swanson et al. |
| 5,800,486 A | 9/1998 | Thome et al. |
| 5,807,395 A | 9/1998 | Mulier et al. |
| 5,830,179 A | 11/1998 | Mikus et al. |
| 5,843,144 A | 12/1998 | Rudie et al. |
| 5,849,011 A | 12/1998 | Jones et al. |
| 5,861,021 A | 1/1999 | Thome et al. |
| 5,871,481 A | 2/1999 | Kannenberg et al. |
| 5,873,877 A | 2/1999 | McGaffigan et al. |
| 5,897,553 A | 4/1999 | Mulier et al. |
| 5,899,932 A | 5/1999 | Dann et al. |
| 5,938,692 A | 8/1999 | Rudie |
| 5,944,715 A | 8/1999 | Goble et al. |
| 5,951,515 A | 9/1999 | Osterlind |
| 5,957,922 A | 9/1999 | Imran |
| 5,964,752 A | 10/1999 | Stone |
| 5,964,756 A | 10/1999 | McGaffigan et al. |
| 5,976,123 A | 11/1999 | Baumgardner et al. |
| 5,987,360 A | 11/1999 | McGrath et al. |
| 5,990,465 A | 11/1999 | Nakaoka et al. |
| 6,007,571 A | 12/1999 | Neilson et al. |
| 6,009,351 A | 12/1999 | Flachman |
| 6,017,358 A | 1/2000 | Yoon et al. |
| 6,017,361 A | 1/2000 | Mikus et al. |
| 6,036,631 A | 3/2000 | McGrath et al. |
| 6,036,713 A | 3/2000 | Kieturakis |
| 6,053,909 A | 4/2000 | Shadduck |
| 6,063,081 A | 5/2000 | Mulier et al. |
| 6,067,475 A | 5/2000 | Graves et al. |
| 6,077,257 A | 6/2000 | Edwards et al. |
| 6,113,593 A | 9/2000 | Tu et al. |
| 6,122,551 A | 9/2000 | Rudie et al. |
| 6,123,083 A | 9/2000 | McGrath et al. |
| 6,147,336 A | 11/2000 | Oshijima et al. |
| 6,148,236 A | 11/2000 | Dann |
| 6,156,036 A | 12/2000 | Sussman et al. |
| 6,161,049 A | 12/2000 | Rudie et al. |
| 6,179,805 B1 | 1/2001 | Sussman et al. |
| 6,179,836 B1 | 1/2001 | Eggers et al. |
| 6,206,847 B1 | 3/2001 | Edwards et al. |
| 6,210,404 B1 | 4/2001 | Shadduck |
| 6,223,085 B1 | 4/2001 | Dann et al. |
| 6,231,591 B1 | 5/2001 | Desai |
| 6,238,389 B1 | 5/2001 | Paddock et al. |
| 6,238,391 B1 | 5/2001 | Olsen et al. |
| 6,238,393 B1 | 5/2001 | Mulier et al. |
| 6,241,702 B1 | 6/2001 | Lundquist et al. |
| 6,258,087 B1 | 7/2001 | Edwards et al. |
| 6,272,384 B1 | 8/2001 | Simon et al. |
| 6,287,297 B1 | 9/2001 | Woodruff et al. |
| 6,302,903 B1 | 10/2001 | Mulier et al. |
| 6,312,391 B1 | 11/2001 | Ramadhyani et al. |
| 6,315,777 B1 | 11/2001 | Comben |
| 6,348,039 B1 | 2/2002 | Flachman et al. |
| 6,398,759 B1 | 6/2002 | Sussman et al. |
| 6,409,722 B1 | 6/2002 | Hoey et al. |
| 6,423,027 B1 | 7/2002 | Gonon |
| 6,440,127 B2 | 8/2002 | McGovern et al. |
| 6,461,296 B1 | 10/2002 | Desai |
| 6,494,902 B2 | 12/2002 | Hoey et al. |
| 6,496,737 B2 | 12/2002 | Rudie et al. |
| 6,508,816 B2 | 1/2003 | Shadduck |
| 6,517,534 B1 | 2/2003 | McGovern et al. |
| 6,524,270 B1 | 2/2003 | Bolmsjo et al. |
| 6,537,248 B2 | 3/2003 | Mulier et al. |
| 6,537,272 B2 | 3/2003 | Christopherson et al. |
| 6,544,211 B1 | 4/2003 | Andrew et al. |
| 6,551,300 B1 | 4/2003 | McGaffigan |
| 6,565,561 B1 | 5/2003 | Goble et al. |
| 6,575,929 B2 | 6/2003 | Sussman et al. |
| 6,575,968 B1 | 6/2003 | Eggers et al. |
| 6,579,270 B2 | 6/2003 | Sussman et al. |
| 6,589,201 B1 | 7/2003 | Sussman et al. |
| 6,607,529 B1 | 8/2003 | Jones et al. |
| 6,638,275 B1 | 10/2003 | McGaffigan et al. |
| 6,640,139 B1 | 10/2003 | Ueberle |
| 6,669,694 B2 | 12/2003 | Shadduck |
| 6,676,628 B2 | 1/2004 | Sussman et al. |
| 6,706,039 B2 | 3/2004 | Mulier et al. |
| 6,716,252 B2 | 4/2004 | Lazarovitz et al. |
| 6,719,738 B2 | 4/2004 | Mehier |
| 6,726,696 B1 | 4/2004 | Houser et al. |
| 6,730,079 B2 | 5/2004 | Lovewell |
| 6,736,810 B2 | 5/2004 | Hoey et al. |
| 6,740,108 B1 | 5/2004 | Just et al. |
| 6,760,616 B2 | 7/2004 | Hoey et al. |
| 6,780,178 B2 | 8/2004 | Palanker et al. |
| 6,827,718 B2 | 12/2004 | Hutchins et al. |

(56) References Cited

U.S. PATENT DOCUMENTS

| | | |
|---|---|---|
| 6,855,141 B2 | 2/2005 | Lovewell |
| 6,887,237 B2 | 5/2005 | McGaffigan |
| 6,905,475 B2 | 6/2005 | Hauschild et al. |
| 6,911,028 B2 | 6/2005 | Shadduck |
| 6,969,376 B2 | 11/2005 | Takagi et al. |
| 6,974,455 B2 | 12/2005 | Garabedian et al. |
| 7,014,652 B2 | 3/2006 | Cioanta et al. |
| 7,041,121 B1 | 5/2006 | Williams et al. |
| 7,066,935 B2 | 6/2006 | Swoyer et al. |
| 7,089,064 B2 | 8/2006 | Manker et al. |
| 7,130,697 B2 | 10/2006 | Chornenky et al. |
| 7,238,182 B2 | 7/2007 | Swoyer et al. |
| 7,247,155 B2 | 7/2007 | Hoey et al. |
| 7,261,709 B2 | 8/2007 | Swoyer et al. |
| 7,261,710 B2 | 8/2007 | Elmouelhi et al. |
| 7,322,974 B2 | 1/2008 | Swoyer et al. |
| 7,328,068 B2 | 2/2008 | Spinelli et al. |
| 7,328,069 B2 | 2/2008 | Gerber |
| 7,335,197 B2 | 2/2008 | Sage et al. |
| 7,340,300 B2 | 3/2008 | Christopherson et al. |
| 7,369,894 B2 | 5/2008 | Gerber |
| 7,429,262 B2 | 9/2008 | Woloszko et al. |
| 7,437,194 B2 | 10/2008 | Skwarek et al. |
| 7,470,228 B2 | 12/2008 | Connors et al. |
| 7,549,987 B2 | 6/2009 | Shadduck |
| 7,865,250 B2 | 1/2011 | Mrva et al. |
| 7,894,913 B2 | 2/2011 | Boggs et al. |
| 7,959,577 B2 | 6/2011 | Schmitz et al. |
| 8,048,069 B2 | 11/2011 | Skwarek et al. |
| 8,216,217 B2 | 7/2012 | Sharkey et al. |
| 8,244,327 B2 | 8/2012 | Fichtinger et al. |
| 8,251,985 B2 | 8/2012 | Hoey et al. |
| 8,272,383 B2 | 9/2012 | Hoey et al. |
| 8,273,079 B2 | 9/2012 | Hoey et al. |
| 8,301,264 B2 | 10/2012 | Achenbach et al. |
| 8,313,485 B2 | 11/2012 | Shadduck |
| 8,372,065 B2 | 2/2013 | Hoey et al. |
| 8,388,611 B2 | 3/2013 | Shadduck et al. |
| 8,409,109 B2 | 4/2013 | Tiesma et al. |
| 8,419,723 B2 | 4/2013 | Shadduck et al. |
| 8,550,743 B2 | 10/2013 | Bonde et al. |
| 8,585,692 B2 | 11/2013 | Shadduck et al. |
| 8,632,530 B2 | 1/2014 | Hoey et al. |
| 8,740,957 B2 | 6/2014 | Masotti |
| 8,801,702 B2 | 8/2014 | Hoey et al. |
| 8,900,223 B2 | 12/2014 | Shadduck |
| 2002/0062123 A1* | 5/2002 | McClurken ............ A61B 18/14 606/34 |
| 2002/0078956 A1 | 6/2002 | Sharpe et al. |
| 2002/0111617 A1 | 8/2002 | Cosman et al. |
| 2002/0177846 A1 | 11/2002 | Mulier et al. |
| 2003/0069575 A1 | 4/2003 | Chin et al. |
| 2003/0092689 A1 | 5/2003 | Escandon et al. |
| 2003/0097126 A1 | 5/2003 | Woloszko et al. |
| 2003/0130575 A1 | 7/2003 | Desai |
| 2003/0206730 A1 | 11/2003 | Golan |
| 2004/0006334 A1 | 1/2004 | Beyar et al. |
| 2004/0068306 A1 | 4/2004 | Shadduck |
| 2004/0186422 A1 | 9/2004 | Rioux et al. |
| 2004/0230316 A1 | 11/2004 | Cioanta et al. |
| 2004/0267340 A1 | 12/2004 | Cioanta et al. |
| 2005/0096629 A1 | 5/2005 | Gerber et al. |
| 2005/0124915 A1 | 6/2005 | Eggers et al. |
| 2005/0149020 A1 | 7/2005 | Jahng |
| 2005/0159676 A1 | 7/2005 | Taylor et al. |
| 2006/0089636 A1 | 4/2006 | Christopherson et al. |
| 2006/0135955 A1 | 6/2006 | Shadduck |
| 2006/0178670 A1 | 8/2006 | Woloszko et al. |
| 2006/0224154 A1 | 10/2006 | Shadduck et al. |
| 2006/0224169 A1 | 10/2006 | Weisenburgh, II et al. |
| 2006/0253069 A1 | 11/2006 | Li et al. |
| 2006/0276871 A1 | 12/2006 | Lamson et al. |
| 2007/0032785 A1 | 2/2007 | Diederich et al. |
| 2007/0038089 A1 | 2/2007 | Hatano et al. |
| 2007/0142846 A1 | 6/2007 | Catanese, III et al. |
| 2007/0179491 A1 | 8/2007 | Kratoska et al. |
| 2007/0197864 A1 | 8/2007 | Dejima et al. |
| 2007/0213703 A1 | 9/2007 | Naam et al. |
| 2008/0021484 A1 | 1/2008 | Catanese, III et al. |
| 2008/0021485 A1 | 1/2008 | Catanese, III et al. |
| 2008/0033232 A1 | 2/2008 | Catanese, III et al. |
| 2008/0033458 A1 | 2/2008 | McLean et al. |
| 2008/0033488 A1 | 2/2008 | Catanese, III et al. |
| 2008/0039833 A1 | 2/2008 | Catanese, III et al. |
| 2008/0039872 A1 | 2/2008 | Catanese, III et al. |
| 2008/0039874 A1 | 2/2008 | Catanese, III et al. |
| 2008/0039875 A1 | 2/2008 | Catanese, III et al. |
| 2008/0039876 A1 | 2/2008 | Catanese, III et al. |
| 2008/0039893 A1 | 2/2008 | McLean et al. |
| 2008/0039894 A1 | 2/2008 | Catanese, III et al. |
| 2008/0046045 A1 | 2/2008 | Yon et al. |
| 2008/0110457 A1 | 5/2008 | Barry et al. |
| 2008/0132826 A1 | 6/2008 | Shadduck et al. |
| 2008/0188811 A1 | 8/2008 | Kim |
| 2008/0208187 A1 | 8/2008 | Bhushan et al. |
| 2008/0214956 A1 | 9/2008 | Briggs et al. |
| 2008/0217325 A1 | 9/2008 | Von Buren et al. |
| 2008/0249399 A1 | 10/2008 | Appling et al. |
| 2008/0262491 A1 | 10/2008 | Swoyer et al. |
| 2008/0269737 A1 | 10/2008 | Elmouelhi et al. |
| 2008/0269862 A1 | 10/2008 | Elmouelhi et al. |
| 2008/0275440 A1 | 11/2008 | Kratoska et al. |
| 2008/0297287 A1 | 12/2008 | Shachar et al. |
| 2008/0312497 A1 | 12/2008 | Elmouelhi et al. |
| 2009/0018553 A1 | 1/2009 | McLean et al. |
| 2009/0054871 A1 | 2/2009 | Sharkey et al. |
| 2009/0118722 A1* | 5/2009 | Ebbers ................ A61B 18/02 606/21 |
| 2009/0138001 A1 | 5/2009 | Barry et al. |
| 2009/0149846 A1* | 6/2009 | Hoey .................. A61B 17/42 606/27 |
| 2009/0199855 A1 | 8/2009 | Davenport |
| 2009/0216220 A1 | 8/2009 | Hoey et al. |
| 2009/0227998 A1 | 9/2009 | Aljuri et al. |
| 2009/0306640 A1 | 12/2009 | Glaze et al. |
| 2010/0016757 A1 | 1/2010 | Greenburg et al. |
| 2010/0049031 A1 | 2/2010 | Fruland et al. |
| 2010/0094270 A1 | 4/2010 | Sharma |
| 2010/0114083 A1 | 5/2010 | Sharma |
| 2010/0179416 A1 | 7/2010 | Hoey et al. |
| 2010/0193568 A1 | 8/2010 | Scheib et al. |
| 2010/0204688 A1 | 8/2010 | Hoey et al. |
| 2010/0256636 A1 | 10/2010 | Fernandez et al. |
| 2010/0262133 A1 | 10/2010 | Hoey et al. |
| 2010/0262137 A1 | 10/2010 | Nye et al. |
| 2010/0286679 A1 | 11/2010 | Hoey et al. |
| 2010/0292767 A1 | 11/2010 | Hoey et al. |
| 2010/0298948 A1 | 11/2010 | Hoey et al. |
| 2011/0060328 A1 | 3/2011 | Skwarek et al. |
| 2011/0077628 A1 | 3/2011 | Hoey et al. |
| 2011/0106072 A1 | 5/2011 | Sundquist et al. |
| 2011/0160648 A1 | 6/2011 | Hoey |
| 2011/0264176 A1 | 10/2011 | Jackson et al. |
| 2011/0319759 A1 | 12/2011 | Liu et al. |
| 2012/0259271 A1 | 10/2012 | Shadduck et al. |
| 2012/0265276 A1 | 10/2012 | Curley |
| 2012/0323167 A1 | 12/2012 | Hoey et al. |
| 2013/0006231 A1 | 1/2013 | Sharma et al. |
| 2013/0066308 A1 | 3/2013 | Landman |
| 2013/0072855 A1 | 3/2013 | Sherry et al. |
| 2013/0074847 A1 | 3/2013 | Hoey et al. |
| 2013/0172867 A1 | 7/2013 | Shadduck et al. |
| 2013/0261692 A1 | 10/2013 | Cardinal et al. |
| 2014/0039356 A1 | 2/2014 | Sachs et al. |
| 2014/0107637 A1 | 4/2014 | Hoey et al. |
| 2014/0200568 A1 | 7/2014 | Sharma |
| 2014/0288543 A1 | 9/2014 | Hoey et al. |
| 2015/0126990 A1 | 5/2015 | Sharma et al. |
| 2015/0157384 A1 | 6/2015 | Hoey et al. |

(56) References Cited

U.S. PATENT DOCUMENTS

| | | |
|---|---|---|
| 2016/0081736 A1 | 3/2016 | Hoey et al. |
| 2017/0056089 A1 | 3/2017 | Hoey et al. |

FOREIGN PATENT DOCUMENTS

| | | |
|---|---|---|
| CN | 101072544 | 11/2007 |
| CN | 101257855 | 9/2008 |
| CN | 101006939 A | 11/2008 |
| CN | 101491458 A | 7/2009 |
| CN | 101803947 A | 8/2010 |
| JP | 7-507696 A | 8/1995 |
| JP | 8-501957 A | 3/1996 |
| JP | 8-504613 A | 5/1996 |
| JP | 11-318925 A | 11/1999 |
| JP | 200014663 A | 1/2000 |
| JP | 2000005191 A | 1/2000 |
| JP | 2001500763 A | 1/2001 |
| JP | 2005137916 A | 6/2005 |
| WO | WO 92/10142 A1 | 6/1992 |
| WO | WO 01/24715 A1 | 4/2001 |
| WO | WO 03/088851 A1 | 10/2003 |
| WO | WO 03/096871 A2 | 11/2003 |
| WO | WO 2006/004482 A1 | 1/2006 |
| WO | WO 2008/083407 A1 | 7/2008 |
| WO | WO2010/080467 A2 | 7/2010 |
| WO | WO2013/160772 A2 | 10/2013 |
| WO | WO2015/089190 A1 | 6/2015 |

OTHER PUBLICATIONS

Hastings et al.; U.S. Appl. No. 15/011,005 entitled "Vapor ablation systems and methods," filed Jan. 29, 2016.

Hastings et al.; U.S. Appl. No. 15/035,944 entitled "Vapor ablation systems and methods," filed May 11, 2016.

Hoey et al.; U.S. Appl. No. 15/154,536 entitled "Systems and methods for treating the bladder with condensable vapor," filed May 13, 2016.

Hoey et al.; U.S. Appl. No. 14/453,254 entitled "Systems and Methods for Treatment of BPH," filed Aug. 6, 2014.

HAI; Photoselective Vaporization Prostatectomy: A Palliative Treatment Option for Men with Urinary Obstruction Secondary to Prostate Cancer; PCRI Prost.Cancer Rsrch.Inst. Reprint.from PCRI Insights Nov. 2005, vol. 8(4); Dwnld from http://www.prostate-cancer.org/pcricms/node/233 on May 10, 2012; 4 pages.

Nguyen et al; Updated results of magnetic resonance imaging guided partial prostate brachytherapy for favorable risk prostate cancer: implications for focal therapy; J. Urol.; 188(4); pp. 1151-1156; Oct. 2012.

Hoey et al.; U.S. Appl. No. 14/773,853 entitled "Systems and methods for treating prostate cancer," filed Sep. 9, 2015.

* cited by examiner

INDUCTION COIL VAPOR GENERATOR

CROSS REFERENCES TO RELATED APPLICATIONS

This Application claims the benefit of U.S. Provisional Patent Application No. 61/619,818, filed Apr. 3, 2012, titled "Induction Coil Vapor Generator", which is incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure generally relates to vapor generation in medical instruments. More specifically, this disclosure relates to induction coil vapor generators in medical instruments.

BACKGROUND

Benign prostatic hyperplasia (BPH) is a common disorder in middle-aged and older men, with prevalence increasing with age. At age 70, more than one-half of men have symptomatic BPH, and nearly 90% of men have microscopic evidence of an enlarged prostate. The severity of symptoms also increase with age with 27% of patients in the 60-70 age bracket having moderate-to-severe symptoms, and 37% of patients in their 70's suffering from moderate-to-severe symptoms.

The prostate early in life is the size and shape of a walnut and weighs about 20 grams. Prostate enlargement appears to be a normal process. With age, the prostate gradually increases in size to twice or more its normal size. The fibromuscular tissue of the outer prostatic capsule restricts expansion after the gland reaches a certain size. Because of such restriction on expansion, the intracapsular tissue will compress against and constrict the prostatic urethra thus causing resistance to urine flow.

BPH is typically diagnosed when the patient seeks medical treatment complaining of bothersome urinary difficulties. The predominant symptoms of BPH are an increase in frequency and urgency of urination. BPH can also cause urinary retention in the bladder which in turn can lead to lower urinary tract infection (LUTI). In many cases, the LUTI then can ascend into the kidneys and cause chronic pyelonephritis, and can eventually lead to renal insufficiency. BPH also may lead to sexual dysfunction related to sleep disturbance or psychological anxiety caused by severe urinary difficulties. Thus, BPH can significantly alter the quality of life with aging of the male population.

BPH is the result of an imbalance between the continuous production and natural death (apoptosis) of the glandular cells of the prostate. The overproduction of such cells leads to increased prostate size, most significantly in the transitional zone which traverses the prostatic urethra.

In early stage cases of BPH, treatments can alleviate the symptoms. For example, alpha-blockers treat BPH by relaxing smooth muscle tissue found in the prostate and the bladder neck, which may allow urine to flow out of the bladder more easily. Such drugs can prove effective until the glandular elements cause overwhelming cell growth in the prostate.

More advanced stages of BPH, however, can only be treated by surgical or minimally invasive tissue ablation interventions. A number of methods have been developed using electrosurgical or mechanical extraction of tissue, and thermal ablation of intracapsular prostatic tissue. In many cases, such interventions provide only transient relief, and there often is significant peri-operative discomfort and morbidity.

SUMMARY OF THE DISCLOSURE

An inductive vapor generator is provided, comprising an outer support assembly, a coil disposed around the outer support assembly, an inner assembly disposed within the outer support assembly, a plurality of microtubes disposed within the inner assembly, the microtubes being configured to receive a fluid from a fluid source, and a RF generator electrically coupled to the coil, the RF generator being configured to apply a current to the coil to inductively heat fluid in the plurality of microtubes to convert the fluid into a heated condensable vapor.

In some embodiments, the outer support assembly comprises a thermally insulating and electrically insulating tube.

In other embodiments, the inner assembly comprises a thermally conductive and electrically insulating tube.

In some embodiments, the generator comprises an air gap between the outer support assembly and the inner assembly.

In one embodiment, the plurality of microtubes comprises stainless steel microtubes.

In some embodiments, the inner assembly comprises a solid metal rod and the plurality of microtubes comprises an array of channels drilled through the solid metal rod.

In one embodiment, the outer support assembly has a length of less than 70 mm.

In another embodiment, the outer support assembly has a diameter of less than 10 mm.

A medical vapor delivery device is also provided, comprising a handle, a working shaft coupled to the handle, an induction vapor generator disposed in the handle and fluidly coupled to a fluid source and the working shaft, the induction vapor generator comprising, an outer support assembly, a coil disposed around the outer support assembly, an inner assembly disposed within the outer support assembly, a plurality of microtubes disposed within the inner assembly, a RF generator electrically coupled to the coil, the RF generator configured to apply a current to the coil, and a controller configured to apply a current to the coil to convert a fluid in the plurality of microtubes into a heated vapor inside the induction vapor generator for delivery of the heated vapor through the working shaft to human tissue.

In some embodiments, the device further comprises a treatment needle disposed near a distal portion of the working shaft.

In some embodiments, the outer support assembly comprises a thermally insulating and electrically insulating tube.

In other embodiments, the inner assembly comprises a thermally conductive and electrically insulating tube.

In some embodiments, the generator comprises an air gap between the outer support assembly and the inner assembly.

In one embodiment, the plurality of microtubes comprises stainless steel microtubes.

In some embodiments, the inner assembly comprises a solid metal rod and the plurality of microtubes comprises an array of channels drilled through the solid metal rod.

In one embodiment, the outer support assembly has a length of less than 70 mm.

In another embodiment, the outer support assembly has a diameter of less than 10 mm.

A method of generating a heated condensable vapor is also provided, comprising injecting a fluid into a plurality of microtubes disposed within an inner tube assembly, applying a current to a coil that is supported by an outer tube assembly, the inner tube assembly being disposed within the outer tube assembly, and inductively heating the fluid within the plurality of microtubes to convert the fluid to a heated condensable vapor.

In some embodiments, the method further comprises insulating the coil from heat with a gap disposed between the inner tube assembly and the outer tube assembly. In one embodiment, the gap comprises an air gap.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

The present disclosure describes methods and apparatus for treating BPH, comprising introducing a heated vapor interstitially into the interior of a prostate, wherein the vapor controllably ablates prostate tissue. This method can utilize vapor for applied energy of between 100 calories and 1,000 calories per lobe in an office-based procedure. In some embodiments, the system includes a vapor delivery mechanism that generates and delivers high quality heated water vapor. The system can utilize a vapor source configured to provide vapor having a temperature of at least 60° C., 80° C., 100° C., 120° C., or 140° C. In some embodiments, the vapor source can comprise an induction coil vapor generator disposed within a vapor delivery device, or alternatively, located outside of the vapor delivery device.

Figure 1:
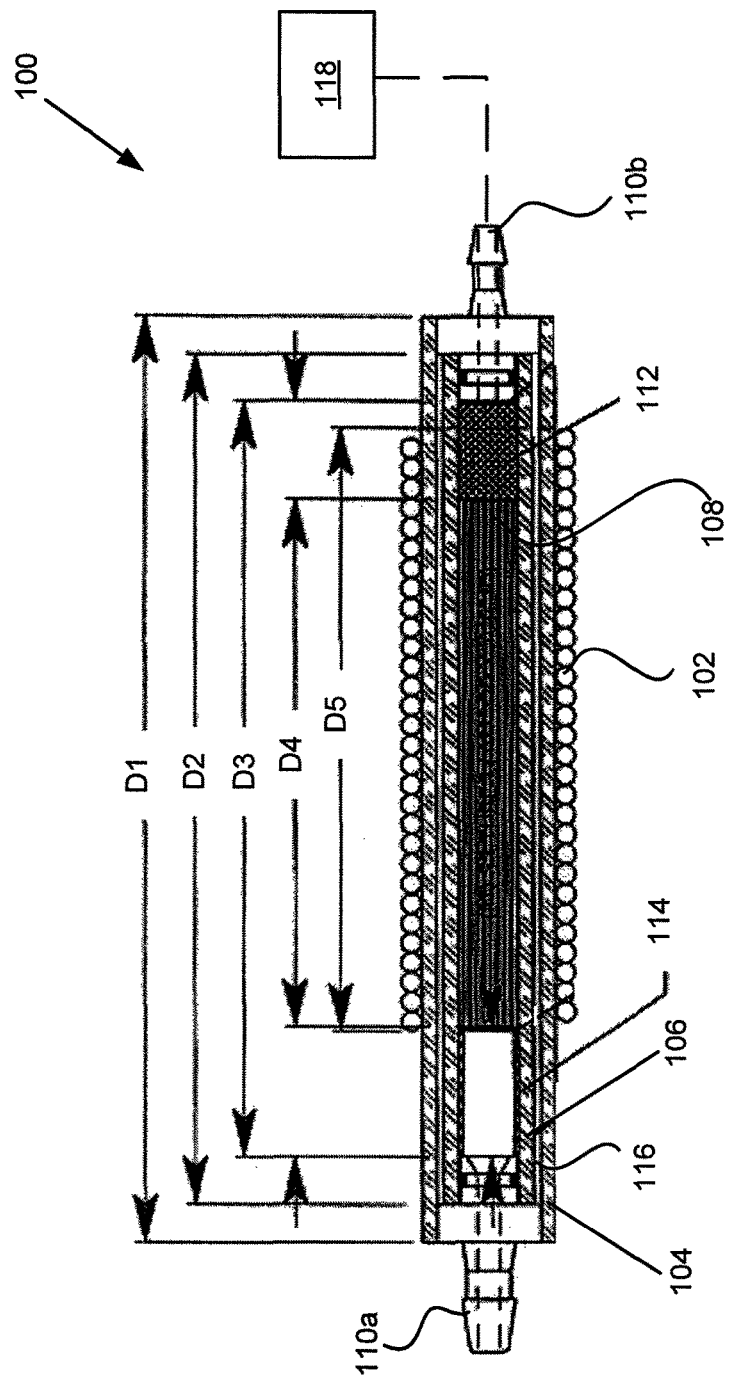
FIG. 1 illustrates an induction coil vapor generator.

FIG. 1 illustrates a cutaway view of an induction coil vapor generator 100 configured to generate a high quality heated condensable vapor. The induction coil vapor generator can include an outer assembly of Litz wire or coiled magnet wire 102 supported by an outer assembly 104, and an inner assembly 106 disposed within the outer assembly. The generator can further include a plurality of metallic microtubes 108 disposed within the inner assembly. The microtubes can be coupled to a fluid source 118.

In some embodiments, the outer assembly can comprise an electrically insulating and thermally insulating material, such as fiberglass, or low density silicone, and the inner assembly can comprise an electrically insulating, thermally conductive material, such as aluminum nitride, alloys of iron including stainless steels, alloys of nickel, alloys of cobalt, quartz, glass, or a ceramic such as aluminum oxide. The outer assembly can be thermally insulating to prevent heat from damaging the coiled magnet wire or from damaging human tissue or other medical device components positioned exterior to the outer assembly. The inner assembly and the microtubes can be thermally conductive so as to inductively heat fluid to convert the fluid into a condensable vapor.

Figure 2:
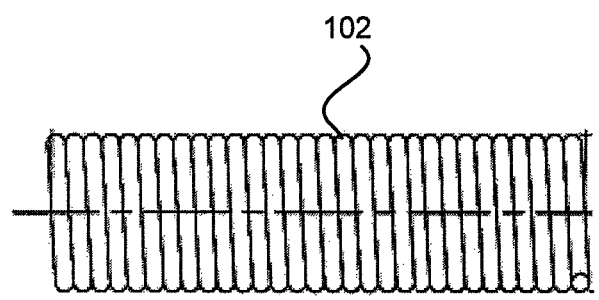
FIG. 2 shows one embodiment of a coiled magnetic wire of the vapor generator.

The coiled magnet wire can comprise any electrically insulated wire, such as insulated copper, silver, gold or aluminum wire used in electromagnets (magnet wire or Litz wire), and can be coupled to a RF generator that produces a current in the coiled magnet wire to generate an inductive field. This inductive field can then be used to heat the inner assembly and/or microtubes to convert fluid in the microtubes into a heated condensable vapor. In one embodiment, the coiled magnet wire comprises 16 gauge copper coil, or magnet wire in the diameter range of 10 AWG to 20 AWG. In another embodiment, the outer assembly is wrapped in magnet wire having 16 AWG and approximately 30.5 turns. The length of the tubes and the gauge and number of wraps of the wire can be adjusted, however, depending on the application and the desired size of the generator, for example with coils in the range of 10 to 100 turns wound with wire in the range 10 to 20 AWG. FIG. 2 shows another view of the coiled magnet wire 102 of FIG. 1.

Referring back to FIG. 1, the inner assembly can house a plurality of metallic microtubes 108, preferably having magnetic permeability larger than 1.5 at the operating frequency of the generator. The plurality of microtubes can comprise an array of 10 to 250 or more metallic microtubes, aligned in a parallel array configured to inductively heat and convert a precisely controlled quantity of sterile water or fluid into a superheated water vapor. Microtubes 108 may have outside diameters ranging from 0.5 mm to 2.5 mm, and inside diameters in the range of 0.25 to 2 mm. The microtubes 108 may be bundled together, preferably tightly enough so that they are in physical contact with each other. They may be physically joined with a metallic material such as solder, or the tubes may simply be long holes drilled through the length of a solid metallic rod.

The microtubes 108 can be encased in inner assembly 106, with O-ring supported pressure-fit caps 110a and 110b sealing both ends of the inner assembly. Cap 110a can be disposed on a distal, vapor emitting end of the generator 100, and cap 110b can be disposed on a proximal, fluid source connecting end of the generator. Liquid water or fluid can flow into the inner assembly and microtubes from a remote fluid source, such as fluid source 118, and the fluid can be inductively heated and converted into condensable vapor when a current is applied to the coiled magnet wire 102 (such as by a RF generator). The parallel array of the microtubes 108 in the inner assembly allows laminar flow of the water/vapor, minimizing back pressure on the fluid source. Heat is transferred efficiently from the inside and outside surfaces of the heated microtubes to the fluid flowing through and between the microtubes because of the large ratio of heated surface area to fluid volume in the microtubes.

In one embodiment, the microtubes can be aligned in parallel with the length of the coiled magnet wire, thereby making them parallel to the inductive magnetic field that is generated when current is applied to the coil. When the tubes are aligned in this fashion, current flows around the circumference of the tubes maximizing the ability of each tube to be heated when an inductive magnetic field is created. As fluid enters the inner assembly and is converted to vapor, the fluid and vapor passes through and between the tubes, thereby contacting both their inner and outer surfaces during the super heating travel from one end of the assembly to the other.

In one embodiment, the idealized expansion ratio of a volume of liquid water converted to pure water vapor is 1760×. This liquid-to-vapor expansion introduces significant mechanical forces even at the small volumes utilized in the inductive vapor generator described above. The most notable mechanical force is back pressure on the fluid source that delivers fluid to the inner assembly and microtubes. Since vapor expansion in a container has no preferred direction, the vapor produced can push backwards as well as forward. The arrangement of the microtubes can minimize the adverse back pressure to allow a syringe pump of normal strength to be used. The microtubes promote laminar flow and also prevent a "core" of liquid water from slipping through the generator by increasing the amount of surface area the water is in contact with. Enhanced contact of the water with the tube surfaces may be achieved by roughening or patterning the tube surfaces to encourage turbulent flow of the water.

Referring still to FIG. 1, in some embodiments, a gap 116 can be provided between the outer assembly and the inner assembly. In this embodiment, the outer assembly 104 is placed over the inner assembly 106, which provides support for the inductive coil, and the gap provides insulation between the inner assembly and both the outer assembly and inductive coil. The air gap can prevent damage to the inductive coil from being secondarily heated by the inner assembly, and retains heat in the inner assembly for more efficient transfer of heat to the water. The gap 116 can comprise only air, or alternatively, the gap can be filled with a gas, fluid, or gel with a low thermal conductivity, such as argon. In this embodiment, since the gap 116 can be used to thermally protect the outer assembly and the coiled magnet wire, it may not be necessary for the outer assembly to be thermally insulating. Thus, in this embodiment, the outer assembly can also comprise quartz, glass, ceramic, in addition to the materials listed above.

In an alternative embodiment, the coiled magnet wire 102 may be wound directly onto the inner assembly 106, placing the outer coil in direct thermal contact with the inner coil assembly. As long as water is being converted to steam in the inner coil assembly 106, the inner coil, and in this embodiment the outer coil, will be maintained at the boiling temperature of water during therapy delivery. Providing that the insulation of the coiled magnet wire or Litz wire of the outer coil can operate at the boiling temperature of water, this is an acceptable embodiment. Commonly used insulation materials can operate to at least 200° C., well above the boiling temperature of water, even at elevated pressures experienced within the heating element. This embodiment may insure repeatable temperatures during therapy and between therapy applications.

The inner assembly can further comprise a sintered filter 112, configured to mechanically aerosolize the fluid as it enters the inner assembly and also to impede backflow, and a spacer tube 114, configured to further increase the ratio of vapor to liquid water before the heated condensable vapor leaves the generator. The sintered filter can comprise a porous disc made of, for example, 316 stainless steel and including very small openings on the order of 10 microns. The spacer tube 114 can comprise a stainless steel tube and can be relatively short compared to the length of the tubes. For example, in one embodiment, the spacer tube is up to approximately 8.5 mm long or 10-15% of the length of the insulating tubes.

In some embodiments, the outer assembly 104 can have a length D1 ranging from 40 mm to 100 mm and a diameter ranging from 4 mm to 25 mm. The inner assembly 106 can have a length D2 ranging from 35 mm to 95 mm and a diameter ranging from 2 mm to 23 mm. The coiled magnet wire 102 can be wound along a length D5 of the outer assembly, ranging from the full length of the outer assembly to only the length of the microtubes 108 (microtube length illustrated by D4). D3 in FIG. 1 illustrates the total length that fluid/vapor travels between end caps 110b and 110a.

Figure 3:
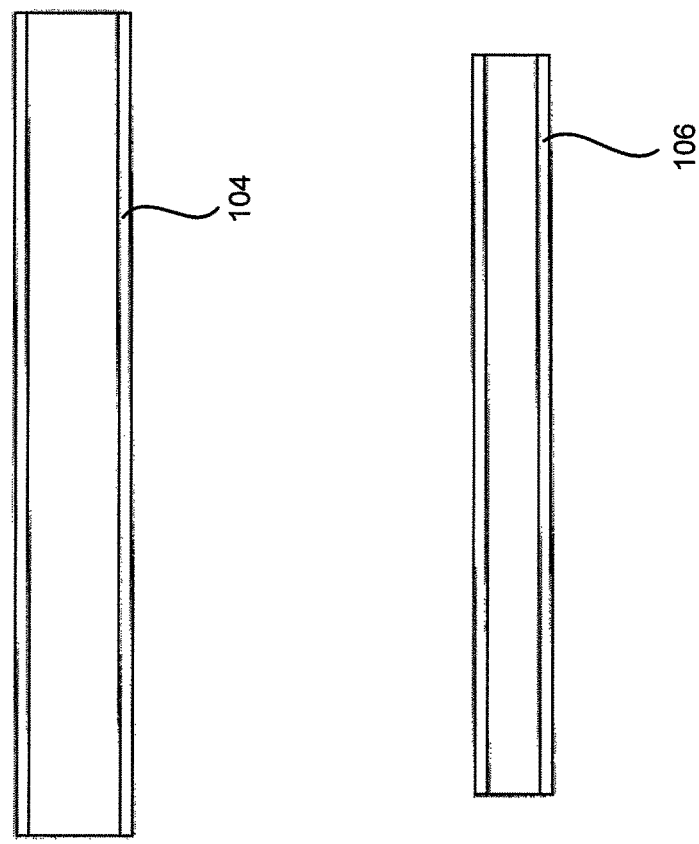
FIG. 3 shows one embodiment of quartz tubes used in the vapor generator.

FIG. 3 illustrates outer and inner assemblies 104 and 106 separate from the rest of the generator assembly. In embodiments incorporating an air gap, when the inner assembly is positioned within the outer assembly, the two tubes can be separated by an air gap of up to 1-5 mm.

In one embodiment, the inner and outer assemblies can be fused quartz, having a low coefficient of thermal expansion, on the order of $0.55 \times 10^{-8}/°$ C., and a temperature strain point of approximately 1070° C. The quartz tubes have a high resistance to thermal shock, and relatively low thermal conductivity (approximately 0.0033 cal cm$^{-1}$ sec$^{-1}$° C. and low dielectric loss factor (<0.0004 at 20° C., 1 MHz). The quartz tubes also have a high tensile strength (approximately 7,000 psi) and a very high compressive strength (approximately $11.1 \times 10^6$ psi).

Figure 4:
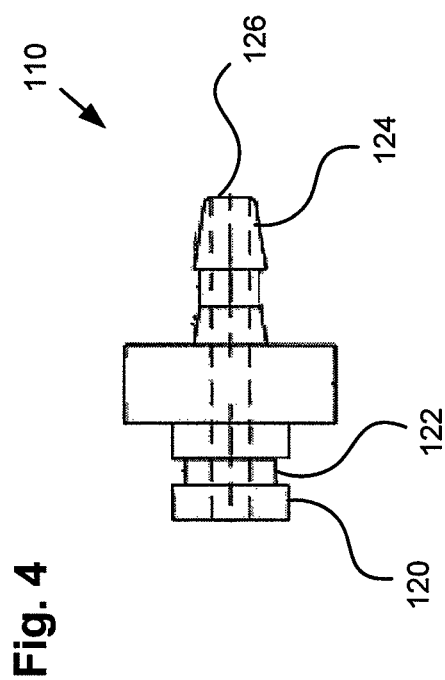
FIG. 4 illustrates one embodiment of a pressure-fit cap of the vapor generator.

FIG. 4 shows a side view of a pressure fit cap 110 (e.g., such pressure fit caps 110a and 110b from FIG. 1). The pressure fit cap can include a proximal portion 120 that can include an o-ring seal 122 and a distal portion 124 that can either connect to the fluid source or pass the exiting vapor. Pressure fit 110 can also include lumens 116 running through the caps to allow for hookup to a fluid source on a proximal end of the generator, and to allow for vapor to exit on a distal end of the generator from the internal assembly. The proximal portion 120 and o-ring seal 122 are configured to mate with an internal surface of the internal assembly (e.g., internal assembly 106 from FIG. 1). The o-ring seal is configured to seal the internal assembly off from the rest of the generator.

Figure 5:
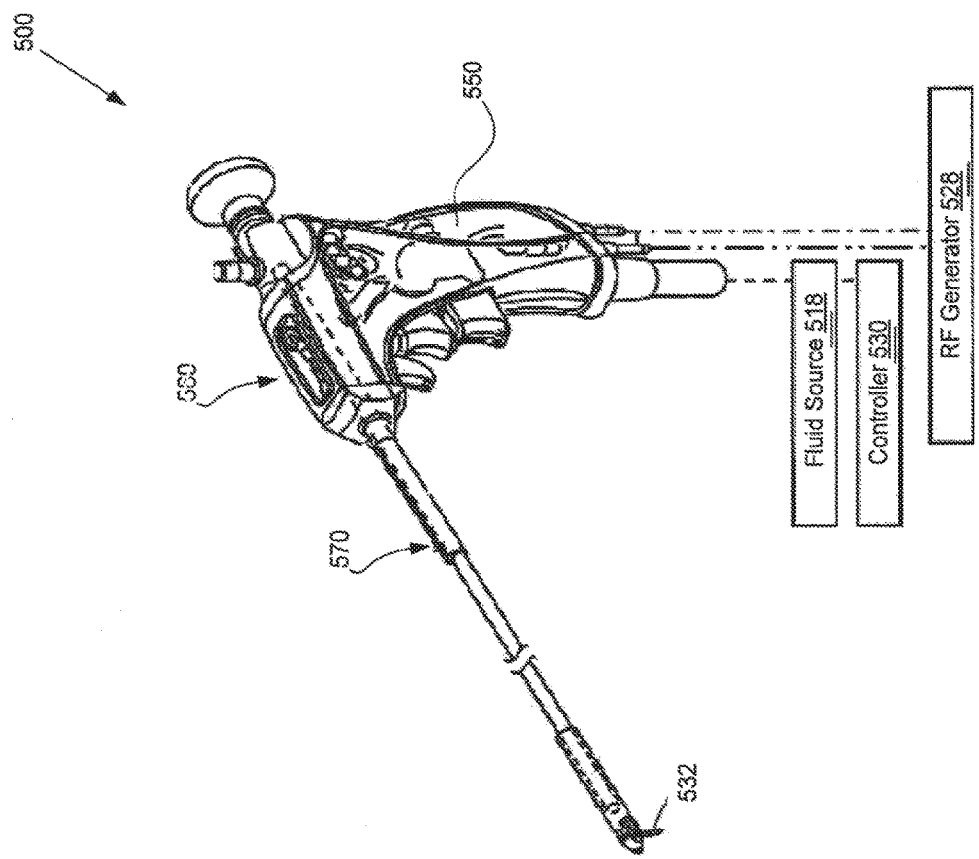
FIG. 5 illustrates one embodiment of a handheld vapor delivery device fitted with the induction coil vapor generator.

The inductive generators described herein can be designed to fit into a handheld vapor delivery device, and integrate with a controller 530, a fluid source 518, and a radiofrequency (RF) generator 528. FIG. 5 illustrates a handheld vapor delivery device 500 fitted with the induction coil vapor generator 100 of FIG. 1. More details of a handheld vapor delivery device as shown in FIG. 5 can be found in U.S. application Ser. No. 13/072,573, which is incorporated herein by reference. In some embodiments, as shown, the vapor generator can be disposed within the device. The vapor generator can be disposed in the handle, as shown by reference 550, or the vapor generator can be disposed in a top portion of the device, as shown by reference 560. In another embodiment, the vapor generator can be disposed inside a shaft of the delivery device, as shown by reference 570. The heated vapor formed by the inductive vapor generator in the device 500 can be coupled to a working shaft or treatment needle 532 of the device to deliver the vapor to human tissue.

In some embodiments, the device 500 is configured for transurethral access to the prostate of the patient. When the distal end of the device is positioned in the prostatic urethra near the prostate, needle 532 can be advanced into the prostate, and vapor generated in the inductive vapor generator can be delivered to the prostate to treat the prostate tissue.

In other embodiments, the vapor generator can be disposed external to the device 500 and can be configured to deliver vapor to the device. A proximal portion of the vapor generator can be fluidly coupled to a fluid source. A distal portion of the vapor generator can be fluidly coupled to the delivery device.

Inductive heating provides fast, consistent heat and can be used in a variety of applications. Inductive heating occurs when an electrically conducting object is exposed to a rapidly changing magnetic field. This is caused by an outer component such as a coil, through which a large high frequency electric current flows. This outer component experiences minimal heating itself due to its low resistance. The passage of current through this coil generates a very intense and rapidly changing magnetic field in the space within the coil. The magnetic field generated by the coil is dependent on the coil current multiplied by the number of coil turns per unit length (ampere turns per meter).

The alternating magnetic field induces a current flow in the inner component, or the metal being heated. The arrangement of the coil and the inner component can be thought of as an electrical transformer, but one in which electrical power transfer is intended to be inefficient, changing the "wasted" electrical energy to heat energy. The coil is the primary winding receiving RF energy from the RF generator and the inner component is like a single turn secondary winding that is short-circuited. This causes high currents (called eddy currents) to flow through the inner component causing it to heat up.

In addition to this, the high frequency used for induction heating gives rise to a phenomenon called skin effect. This skin effect forces the induced alternating current to flow in a thin layer towards the surface of the inner component. The skin effect increases the effective resistance of the metal to the passage of the large current. Therefore it greatly increases the heating effect caused by the current induced in the workpiece. On the other hand, the skin effect may adversely increase the resistance of the coiled magnet wire 102.

For ferrous metals like iron and some steels, the magnetic permeability of the inner coil material can enhance or magnify the magnetic field generated by the coiled magnet wire 102, thereby increasing the magnitude of the eddy currents and inductive heating of the inner coil for a given current flowing in the outer coiled wire. There is an additional heating mechanism that takes place in ferromagnetic materials at the same time as the eddy currents mentioned above. These intense magnetic fields inside the coil repeatedly magnetize and de-magnetize the iron crystals. This rapid flipping of the magnetic domains causes considerable friction and heating inside the material. Heating due to this mechanism is known as Hysteresis loss. For these reasons, ferrous materials having magnetic properties lend themselves more easily to induction heating than those without magnetic properties.

Unlike direct resistive heating, the current coming directly from the power source never directly contacts the material being heated. Instead, it is transformed first to a magnetic field, then as that magnetic field affects the conduction in the inner component, back to a self-contained secondary electric circuit.

Direct resistive heating is also capable of making water vapor, in some applications. However, arcing and plating are inescapable by-products of using direct resistive heating and the consequences (deterioration of electrodes, etc.) create great difficulties in controlling such vapor for precision applications.

Several parameters must be balanced in an induction generator design to improve the quality of the vapor being generated. These parameters include, but are not limited to: magnet wire coil impedance, frequency of driving RF energy, composition of materials being heated, geometry of internal components, management of mechanical forces, and RF source impedance matching (including C-matching network).

Inductance in the coil can be increased by adding more turns to the wire coil, increasing the coil diameter, and shortening the length of the coil. However, increasing inductions via each of these examples may also come with some consequences. For example, adding more turns to the wire coil (where the coil maintains the same coil length) requires a thinner coil wire, which increases the resistive heating in the outer coil component. This is one of the consequences that the use of inductive heating is designed to prevent.

In one example of the coil in FIG. 2, constructed with 16 AWG magnet wire, the resistance is about 0.013 Ohms at DC. The resistance of copper increases with frequency due to the skin effect. However, if the 16 AWG wire is made from insulated strands of smaller diameter wire, i.e. Litz wire, such that the diameter of the individual strands of wire are smaller than twice the skin depth at the operating frequency, this increase of resistance with frequency can be avoided. When a typical rms current of about 17 amps is applied, the Ohmic heat generated in the coil is about 4 Watts, which can be readily dissipated in the hand piece of the device of FIG. 5. Other coil designs may create excessive heating of the coil. The resistance of the coil increases with increasing temperature, further increasing heat generation for a fixed current and fixed magnetic induction within the coil. If a constant induction is maintained, coil temperatures may rapidly rise beyond the temperature for which the coil insulation degrades. If a fixed input power is maintained, resistive heating in the outer coil reduces the amount of electrical energy being used to generate the required magnetic field, causing in turn less ability to heat the inner component. Coil resistance can be minimized to acceptable levels if coil resistance can be at least 100 times smaller than inductive resistance. When the coil of FIG. 2 is operated at 250 kHz, the ratio of inductive reactance to coil resistance can be larger than unity and may be as large as about 280.

A larger coil diameter causes the generator unit to increase in size, and reduces the magnetic coupling to the inner heated component which can cause efficiency reduction. If the inner heated component is made larger to compensate, the vapor inside this larger space must be reduced proportionally more to enter the treatment needle, which can cause turbulent flow. This also causes back pressure on the syringe pump delivering liquid water to be converted to vapor, and may even cause condensation.

Shortening the length of the assembly means a shorter length for the inner, heated component. As the ability to convert liquid water to vapor is directly proportional to the surface area of the heated inner component that the water can contact, and a shorter assembly of the same design will always have less surface area, a shorter assembly will be less able to completely and consistently create vapor.

Figure 6:
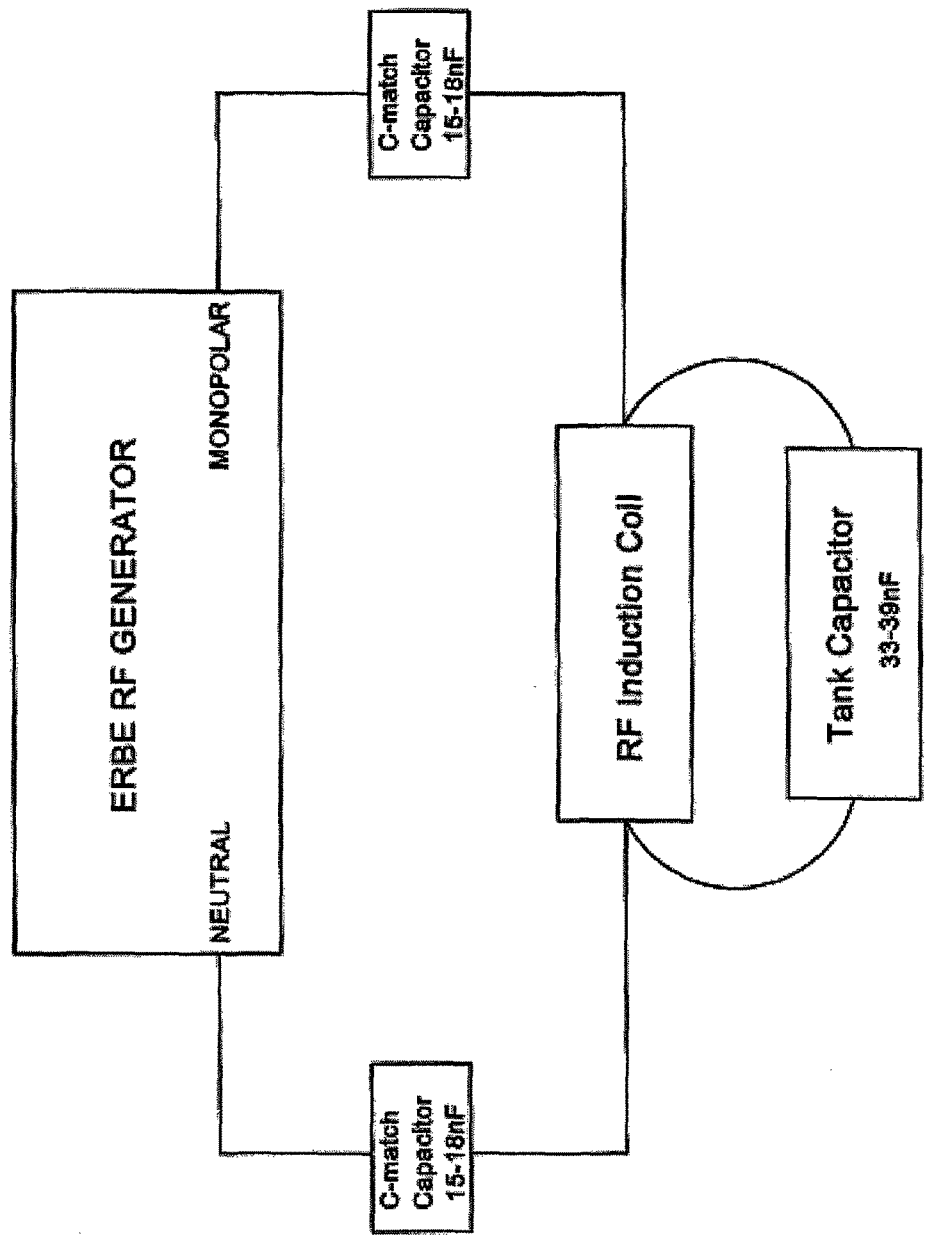
FIG. 6 is a flowchart illustrating one embodiment of an induction coil vapor generator system.

FIG. 6 illustrates a schematic diagram of a system including an RF generator, a C-matching network, and an induction coil (as described above). Greater inductive power results in more inductive heating if all other factors are constant, and greater inductive power can be achieved by applying more current to the generator. However, if the inductive coil portion of the load acts to absorb power, it can cause resistive heating in the coil. If the coil has low impedance, however, the residual power exiting the coil will impact power coming in the opposite direction during each cycle of the polarity (vector) shift. The trade-off between these factors leads to the importance of a proper impedance matching network.

In electronics, impedance matching is the practice of designing the input impedance of an electrical load or the output impedance of its corresponding signal source in order to maximize the power transfer and/or minimize reflections from the load. In the vapor generator described above, a higher frequency is advantageous since only the inductive microtubes need to be heated in order to convert liquid to vapor. A high frequency combined with a load resistance in the wire coil causes the impedance of the generator to become primarily reactive, which calls for complex conjugate mapping and C-matching.

In the generator above, the wire coil is made to resonate at the intended operating frequency by way of a capacitor placed in parallel with the coil. This parallel resonance recaptures the current exiting the coil, both preventing the current from being reflected against incoming current in the opposite direction during polarity shift and magnifying the current through the work coil compared to the output current capability of the RF generator alone. In this case, the RF generator only has to provide the part of the load current that actually does real work and is lost by converting electrical energy to heat, not the full circulating current in the coil.

The parallel resonant circuit can make a tenfold reduction in the current that must be supported by the RF generator and the wires connecting it to the coil. Conduction losses are typically proportional to current squared, so a tenfold reduction in load current represents a significant saving in conduction losses in the RF generator and associated wiring.

In a parallel resonant tank circuit the coil can be thought of as an inductive load with a power factor correction ("PFC") capacitor connected across it. As connecting a capacitor would normally shift current and voltage 90 degrees out of phase to each other, the PFC capacitor is chosen with specifications to provide a reactive current flow equal and opposite to the large inductive current drawn by the coil. This cancels the phase shift effect and brings voltage and current back into phase for maximum power. Therefore, the only real current flow from the RF generator is the relatively small amount required to overcome losses in the PFC capacitor and coil.

Large eddy currents flowing on the surface of the induction tubes are required in order to heat the inductive microtubes. It is the job of the matching network and the coil itself to transfer a high voltage, low current from the RF generator to the low voltage, high current required to heat the induction tubes efficiently.

Figure 7A:
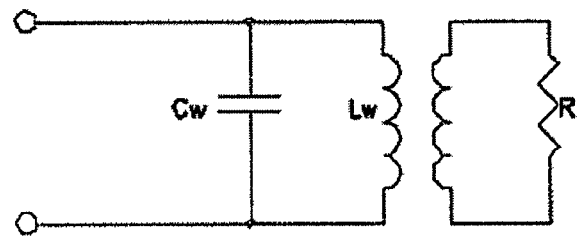
FIGS. 7A-7C illustrate various matching networks for matching an RF generator to an induction vapor generator.

Referring to FIG. 7A, when thinking of the tank circuit incorporating the work coil ($L_W$) and its capacitor ($C_W$) as a parallel resonant circuit. The circuit has a resistance (R) due to the resistive vapor generator coupled into the work coil and due to the magnetic coupling between the two conductors. In practice, the resistance of the work coil, the resistance of the tank capacitor, and the reflected resistance of the vapor tubes all introduce a loss into the tank circuit and damp the resonance. Therefore it is useful to combine all the losses into a single "loss resistance."

Figure 7B:
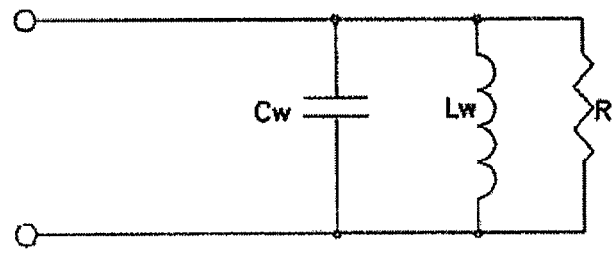

In the case of a parallel resonant circuit, this loss resistance appears directly across the tank circuit. This resistance represents the only component that can consume real power, and therefore this can be considered as the load which power is being driven into in an efficient manner, as shown in FIG. 7B.

When driven at resonance, the current drawn by the tank capacitor and the work coil are equal in magnitude and opposite in phase and therefore cancel each other out as far as the source of power is concerned. This means that the only load seen by the RF generator at the resonant frequency is the loss resistance across the tank circuit. This loss resistance is quite low, however. The resistance of either the coil or capacitor alone would be low to begin with, and by being placed in parallel, the combined resistance is lowered even further. This places the combined load (coil and tank capacitor) even further away from the impedance for which the RF generator is optimized with its own impedance. For any RF generator attached to a real world load, the power delivered from the output terminal already has current and voltage out of phase, with the presumption that an operator will use a load closely matched to this RF generator impedance.

In the case of the vapor generator, the parallel resonant tank circuit is important, as it recirculates power that otherwise would exit the low impedance load and be reflected, but the low impedance of the combined load is even less matched to the generator, and recirculation of out-of-phase current and voltage takes them more out of phase.

The job of the C-matching network is to move delivered current and voltage back into phase and transform the relatively low loss resistance across the tank circuit up to a higher value that better suits the RF generator. This is as simple as placing the proper capacitor in series between the RF generator and coil.

Figure 7C:
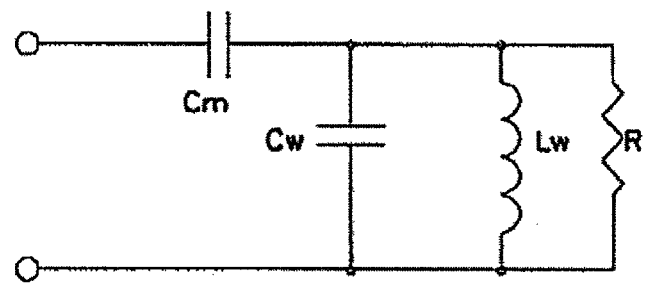

Referring to FIG. 7C, the C-match network comprises capacitor $C_m$ and $L_m$ (not shown). $L_m$ and $L_w$ are in parallel, however, the work coil is assumed to be the combination of both inductors. $C_w$ is adjusted for maximum voltage across the coil before $C_m$ is connected to the circuit. Once connected, $C_m$ is adjusted for the highest voltage across the coil.

Figure 8A:
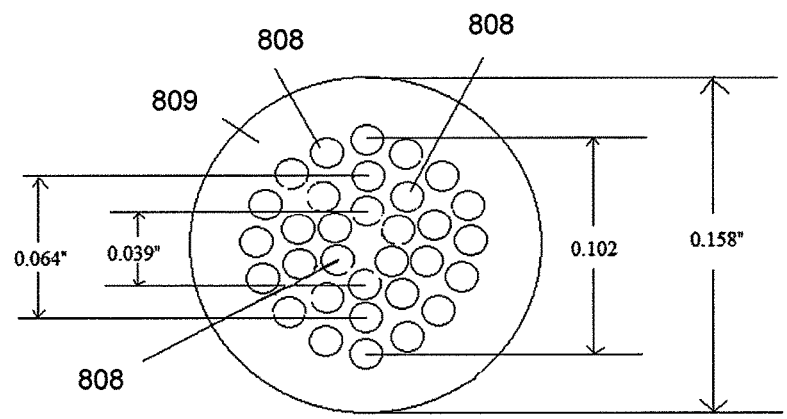
FIGS. 8A-8C illustrate another embodiment of a vapor generator.
Figure 8B:
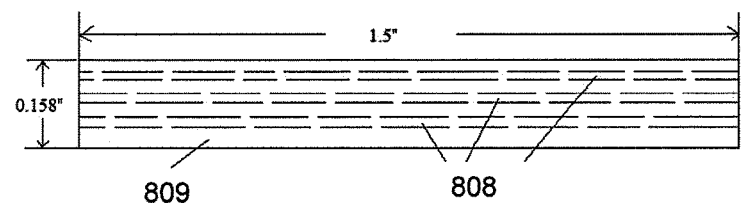
Figure 8C:
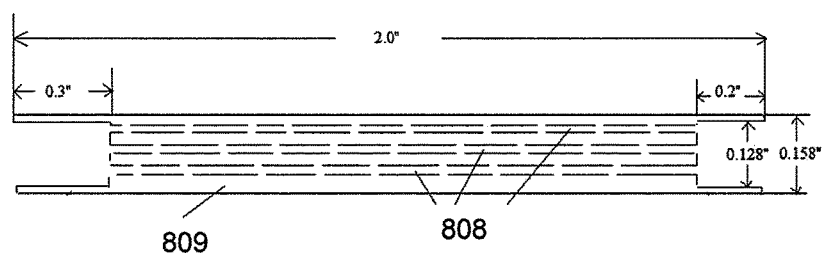

In the embodiments, described above, the generator is formed from outer and inner assemblies comprising hollow tubes. In an alternative embodiment, the generator can be constructed from a solid metal rod with holes drilled through the length of the rod, as shown in FIGS. 8A-8C. FIG. 8A illustrates a cross sectional view of holes/tubes 808 drilled through the length of a solid metal rod 809, and FIG. 8B shows a side view of the rod. In the embodiment of FIG. 8C, the ends of the rod may be drilled out to form a proximal tubular space for hook up to a water line, and a distal tubular space for sintered filter, an expansion space, and a vapor line fitting. The solid metal rod with holes drilled through the length of the rod of FIGS. 8A-8C can replace the microtubes of FIG. 1, for example.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. An inductive vapor generator, comprising:
   an outer support assembly comprising a first tube wherein the first tube is thermally insulating and electrically insulating;
   a coil disposed around the outer support assembly;
   an inner assembly comprising a second tube, the inner assembly being disposed within the outer support assembly wherein the second tube is thermally conductive and electrically insulating;
   a plurality of microtubes disposed within the inner assembly, the plurality of microtubes being configured to receive a fluid from a fluid source;
   a first cap pressure-fit on a first end of the inner assembly and a second cap pressure-fit on a second end of the inner assembly, wherein each of the first and the second pressure-fit caps includes an o-ring seal;
   a sintered filter disposed within the inner assembly; and
   a radiofrequency generator electrically coupled to the coil, the radiofrequency generator being configured to apply a current to the coil to inductively heat the fluid in the plurality of microtubes to convert the fluid into a heated condensable vapor.

2. The inductive vapor generator of claim 1 further comprising a gap between the outer support assembly and the inner assembly.

3. The generator of claim 2 wherein the gap is filled with argon.

4. The inductive vapor generator of claim 1 wherein the plurality of microtubes comprises stainless steel microtubes.

5. The inductive vapor generator of claim 1 wherein the outer support assembly has a length of less than 70 mm.

6. The inductive vapor generator of claim 1 wherein the outer support assembly has a diameter of less than 10 mm.

7. The inductive vapor generator of claim 1 wherein the sintered filter comprises a stainless steel disc.

8. The inductive vapor generator of claim 7 wherein the sintered filter includes a plurality of openings, wherein each of the plurality of openings measures approximately 10 microns.

9. The inductive vapor generator of claim 1 further comprising a first capacitor connected in series between the radiofrequency generator, and the coil and a second capacitor connected in parallel with the coil.

10. A medical vapor delivery device, comprising:
    a handle;
    a working shaft coupled to the handle;
    an induction vapor generator disposed in the handle and fluidly coupled to a fluid source and the working shaft, the induction vapor generator comprising:
      an outer support assembly comprising a first tube wherein the first tube is electrically insulating;
      a coil disposed around the outer support assembly;
      an inner assembly comprising a second tube, the inner assembly being disposed within the outer support assembly wherein the second tube is electrically insulating;
      a plurality of microtubes disposed within the inner assembly; and
      a first cap pressure-fit on a first end of the inner assembly and a second cap pressure-fit on a second end of the inner assembly, wherein each of the first and the second pressure-fit caps includes an o-ring seal;
    a radiofrequency generator electrically coupled to the coil, the radiofrequency generator configured to apply a current to the coil; and
    a controller configured to apply a current to the coil to convert a fluid in the plurality of microtubes into a heated vapor inside the induction vapor generator for delivery of the heated vapor through the working shaft to human tissue.

11. The medical vapor delivery device of claim 10 further comprising a treatment needle disposed near a distal portion of the working shaft.

12. The medical vapor delivery device of claim 10 wherein the first tube is thermally insulating and wherein the second tube is thermally conductive.

13. The medical vapor delivery device of claim 12 further comprising a gap between the outer support assembly and the inner assembly.

14. The generator of claim 13 wherein the gap is filled with argon.

15. The medical vapor delivery device of claim 10 wherein the plurality of microtubes comprises stainless steel microtubes.

16. The medical vapor delivery device of claim 10 wherein the outer support assembly has a length of less than 70 mm.

17. The medical vapor delivery device of claim 10 wherein the outer support assembly has a diameter of less than 10 mm.

* * * * *